(12) United States Patent
Hiraishi et al.

(10) Patent No.: US 7,871,600 B2
(45) Date of Patent: Jan. 18, 2011

(54) HAIR CARE COMPOSITION

(75) Inventors: Takahiro Hiraishi, Haga-gun (JP); Stuart Keith Pratley, Wirral (GB); Aart van Vuure, Randwijk (NL)

(73) Assignee: Conopco Inc., Englewood Cliffs, NJ (US)

( * ) Notice: Subject to any disclaimer, the term of this patent is extended or adjusted under 35 U.S.C. 154(b) by 539 days.

(21) Appl. No.: 11/660,489

(22) PCT Filed: Jun. 28, 2005

(86) PCT No.: PCT/EP2005/007018

§ 371 (c)(1), (2), (4) Date: Feb. 16, 2007

(87) PCT Pub. No.: WO2006/018065

PCT Pub. Date: Feb. 23, 2006

(65) Prior Publication Data

US 2007/0264220 A1 Nov. 15, 2007

(30) Foreign Application Priority Data

Aug. 17, 2004 (EP) .................. 04254920

(51) Int. Cl.
- A61K 8/92 (2006.01)
- A61K 8/31 (2006.01)
- A61K 8/97 (2006.01)
- A61K 5/06 (2006.01)
- A61K 8/72 (2006.01)
- A61Q 5/12 (2006.01)

(52) U.S. Cl. ................. 424/70.11; 424/70.1; 424/70.31; 424/74; 424/70.12

(58) Field of Classification Search .................. None
See application file for complete search history.

(56) References Cited

U.S. PATENT DOCUMENTS

| | | | | |
|---|---|---|---|---|
| 4,350,605 A | * | 9/1982 | Hughett | 516/7 |
| 4,524,787 A | * | 6/1985 | Khalil et al. | 132/204 |
| 4,664,820 A | * | 5/1987 | Magauran et al. | 508/136 |
| 5,116,607 A | | 5/1992 | Jones | 424/70 |
| 6,132,736 A | | 10/2000 | Mellul et al. | 424/401 |
| 6,656,487 B2 | * | 12/2003 | Afriat et al. | 424/401 |
| 2001/0029242 A1 | | 10/2001 | Chandra | 510/119 |
| 2002/0122811 A1 | | 9/2002 | Stein et al. | 424/401 |
| 2003/0053971 A1 | | 3/2003 | Carson et al. | 424/70.1 |
| 2003/0118621 A1 | * | 6/2003 | Heidenfelder et al. | 424/401 |
| 2004/0018250 A1 | * | 1/2004 | Ceccoli et al. | 424/725 |
| 2004/0120918 A1 | * | 6/2004 | Lintner et al. | 424/70.14 |
| 2005/0169877 A1 | * | 8/2005 | Grollier et al. | 424/70.31 |

FOREIGN PATENT DOCUMENTS

| | | |
|---|---|---|
| EP | 0868898 | * 10/1998 |
| EP | 0 868 898 | 9/2003 |
| WO | 02/43671 | 6/2002 |
| WO | 03/032930 | 4/2003 |

* cited by examiner

*Primary Examiner*—Yvonne L Eyler
*Assistant Examiner*—Sarah Al-Awadi
(74) *Attorney, Agent, or Firm*—Karen E. Klumas

(57) ABSTRACT

A leave on hair care composition comprising a) a wax dispersion; and b) an aqueous oil emulsion wherein the oil phase is a liquid and comprises: i) one or more non-volatile oils, where the dynamic viscosity of any single non-volatile oil or the dynamic viscosity of a blend of non-volatile oils is less than 1000 mPa·s at 35° C. and 5 s-1; ii) an oil dispersible structurant such that the dynamic viscosity of the structured oil phase at 35° C. prior to formation of the emulsion is at least 50,000 mPa·s at a shear rate of 0.5 s-1 and is less than 6,000 mPa·s at a shear rate of 500 s-1.

15 Claims, No Drawings

HAIR CARE COMPOSITION

FIELD OF THE INVENTION

This invention relates to hair care compositions, in particular to hair care compositions that style hair.

BACKGROUND AND PRIOR ART

Hair styling products are widely used and are usually applied in the form of, sprays, mousses, gels and lotions. A major disadvantage with using styling creams is that they have a tendency to feel sticky both in the pot before styling, on the hands when applying and on the hair after styling.

Hair Care

Formulations containing waxes and oils are described in EP 0 868 898 (Shiseido & Co, JP), US 2002/122811 (Stein Bernd at al) and U.S. Pat. No. 5,116,607 (Jones et al).

The present invention is a hair styling cream that helps mitigate the problem of stickiness and yet gives good styling hold.

Further advantages of the creams of the present invention are: they can be used to maintain a style; enable re-styling of hair; condition hair; reduce hair damage; provide hair shine; provide a wet look; control hair volume and align the hair.

DESCRIPTION OF THE PRESENT INVENTION

Accordingly the present invention relates to a leave on hair care composition comprising:

a) a wax dispersion; and b) an aqueous oil emulsion wherein the oil phase is a liquid and comprises:
  i) one or more non-volatile oils, where the dynamic viscosity of any single non-volatile oil or the dynamic viscosity of a blend of non-volatile oils is less than 1000 mPa·s at 35° C. and 5 s$^{-1}$;
  ii) an oil dispersible structurant such that the dynamic viscosity of the structured oil phase at 35° C. prior to formation of the emulsion is at least 50,000 mPa·s at a shear rate of 0.5 s$^{-1}$ and is less than 6,000 mPa·s at a shear rate of 500 s$^{-1}$.

The invention also relates to a method of styling hair by applying to the hair a composition as described above.

The invention also relates to the use of a hair composition as described above for styling hair, maintaining a style, enabling re-styling of hair, conditioning hair, reducing hair damage, providing hair shine, providing a wet look and/or controlling hair volume or alignment.

The invention also describes a manufacturing process for a hair cream comprising the steps of:

i) selecting a non-volatile oil or oils, where the dynamic viscosity of any single non-volatile oil or the dynamic viscosity of a blend of non-volatile oils is less than 1000 mPa·s at 35° C. and 5 s$^{-1}$;

ii) adding to the oil an oil dispersible structurant to form a structured oil phase such that the dynamic viscosity of the structured oil phase at 35° C. prior to formation of the emulsion is at least 50,000 mPa·s at a shear rate of 0.5 s$^{-1}$ and is less than 6,000 mPa·s at a shear rate of 500 s$^{-1}$ forming an emulsion with the structured oil phase and;

iii) adding a wax to the resulting structured oil and heating;

iv) adding aqueous components to create an emulsion; and v) cooling the product.

DETAILED DESCRIPTION OF THE INVENTION

Although the composition may be any leave on formulation it is preferable if it is in the form of a cream. In the context of the present invention a cream is defined as not immediately pourable under gravity.

It is preferable if the dynamic viscosity of the final composition is from 2,000 to 300,000 mPa·s at 5 s$^{-1}$ and 25° C., more preferably from 10,000 to 300,000 mPa·s, most preferably from 20,000 to 200,000 mPa·s. It is highly preferable if the dynamic viscosity is from 30,000 to 150,000 mPa·s The dynamic viscosity of the fluids was determined with a standard stress controlled rheometer (this case Carrimed CSL-100), using a parallel plate configuration at a gap height of 200 μm and by measuring dynamic viscosity at a range of shear rates.

The Wax

A wax is present in the invention as a wax dispersion. In the context of the present invention a wax can be defined as a high melting point oil, that is an oil with a melting point above 45° C., preferably above 55° C.

The level of wax in the composition is preferably from 5 to 60% by weight of the total composition more preferably from 20 to 50% by weight most preferably from 30-45% by weight.

Preferred waxes include fatty alcohols and fatty acid that are solid at room temperature, particularly preferred are paraffin wax, triglyceride or mixtures thereof. Most preferred are microcrystalline wax and bees wax.

The Oil Phase

It is advantageous, for styling hair, if the oil phase at 35° C. prior to addition to the cream has a yield stress of at least 500 Pa, preferably a yield stress of at least 1,000 Pa.

The yield stress of a fluid is defined as the critical stress at which a sharp drop in dynamic viscosity is observed.

It is also preferable if the oil phase prior to formation of the emulsion when sheared to a point past its yield point has a recovery ratio of at least 5%, more preferably at least 10% and most preferably at least 15%.

The recovery ratio of the structured oil phase is defined in the context of the present invention as the dynamic viscosity of the oil phase at a shear rate of 0.5 s$^{-1}$ after having been sheared beyond its yield stress (the maximum shear rate used to induce yield was 500 s$^{-1}$), normalised to the dynamic viscosity of the oil phase at a shear rate of 0.5 s$^{-1}$ before having been sheared beyond its yield point. Thus the measuring protocol was to measure the dynamic viscosity whilst ramping up the shear rate from 0.5 s$^{-1}$ to 500 s$^{-1}$ over a period of 5 minutes, immediately followed by a shear rate ramp down from 500 s$^{-1}$ to 0.5 s$^{-1}$ over 5 minutes.

It should be noted that in this invention it is preferable if the wax is present in a separate dispersed phase to the aqueous emulsion phase. However it should be noted that in some cases some of the wax present may reside in the emulsified oil. Preferably no more than 30 wt % of the wax will be present in the emulsified oil, more preferably no more than 10 wt % of the total wax present.

It is particularly advantageous if the wax and the non-volatile oil are of a different chemical class. An example of this would a paraffin wax and a triglyceride oil.

Non-Volatile Oils

The composition comprises one or more non-volatile oils, where the dynamic viscosity of any single non-volatile oil or the dynamic viscosity of a blend of non-volatile oils is less than 1000 mPa·s at 35° C. at 5 s$^{-1}$. Preferably the dynamic viscosity is less than 500 mPa·s at 35° C. at 5 s$^{-1}$, more preferably less than 100 mPa·s, most preferably less than 50 mPa·s.

The non-volatile oils have a melting point of less than 40° C., preferably less than 35° C.

A non-volatile oil is defined such that when the oil is placed in a petri-dish in a room at standard environmental conditions (20° C., 50% RH) at a fluid height of 3 mm, after 1 hour less than 10 wt % of the emollient will have evaporated.

Oils can be selected from the group consisting of triglycerides, fatty esters, fatty alcohols, fatty acids or mineral oils (branched hydrocarbons) and mixtures thereof.

Preferably the non-volatile oil is selected from the group consisting of triheptanoin, tricaprylin, tricaprin, triundecanoin, trilinolein, triolein, almond oil, coconut oil, olive oil, palm kernel oil, peanut oil, sunflower oil, isopropylmyristate, isopropylpalmitate, isocetyl stearate, ethyl oleate, octyl isostearate, butyl myristate, butyl stearate, octyl palmitate, ethylhexyl cocoate, octyl dodecanol, oleyl alcohol, isostearyl alcohol, isostearic acid, mineral oil, paraffin oil, dicaprylate/dicaprate propylene glycol, C12-15 alkyl benzoate and derivatives or mixtures thereof. Particularly preferred is tricaprylin.

Suitable mineral oils are those sold under the name Sirius White Oils by Fuchs Lubricants (UK). Examples of suitable oils are Sirius M85, Sirius M125 and Sirius M350.

Other suitable oils are silicone oils, for example dimethicone, with dynamic viscosity as previously defined.

The level of the oil phase within the total composition is preferably greater than 10 wt % of the total composition, more preferably greater than 20 wt %. Preferred ranges of oil phase in the composition are from 5 to 50% by weight of the total composition, more preferably from 10 to 40 wt %, most preferably from 15 to 30 wt %.

Oil Structurant

The structurant is oil dispersible.

Suitable structurants are selected from the group consisting of dextrin palmitate, trihydroxystearin, hydroxy stearic acid, hydrophilic or hydrophobic silica or preferably a hydrophobically modified clay such as stearalkonium hectorite, quaternium-18 bentonite, quaternium-18 hectorite or disteardimonium hectorite and derivatives or mixtures of these.

If the structurant is a hydrophobically modified clay, such as stearalkonium hectorite, it is preferable if the oil phase further contains a polar activator. A polar activator polarises the edges of the hydrophobically modified clay platelets so the clay platelets form a network structure when dispersed in oil through polar interaction. Suitable polar activators are propylene carbonate in about 5 wt % water or an ethanol/water 95:5 mixture.

The structurant should be chosen such that the dynamic viscosity of the structured oil phase at 35° C. prior to addition to the emulsion is at least 50,000, more preferably at least 100,000, most preferably at least 250,000 mPa·s at a shear rate of 0.5 s$^{-1}$, and is less than 6,000, more preferably less than 4,000, most preferably less than 2,000 mPa·s at a shear rate of 500 s$^{-1}$. A highly preferred oil phase has a dynamic viscosity at 35° C. of at least 500,000 mPa·s at a shear rate of 0.5 s$^{-1}$ and a dynamic viscosity of 1,000 mPa·s or less at a shear rate of 500 s$^{-1}$.

The level of structurant within the oil phase is from 0.5 to 20 wt % of the total oil content in the formulation.

Surfactant System

The compositions of the invention are Oil-in-Water emulsions and require a suitable surfactant system to emulsify the structured oil material.

Particularly suitable for this purpose are non-ionic surfactants. To obtain an Oil-in-Water emulsion it is desirable to use a surfactant system with a high HLB (Hydrophilic to Lipophilic Balance) value. It is particularly desirable in this case to use a mixture of a high HLB surfactant and a low HLB surfactant.

There are many suitable non-ionic surfactant systems, but particularly preferred is a surfactant mixture of 80% polyoxyethylene sorbitan monostearate (20 EO) and 20% sorbitan monostearate.

Styling Compound

In some aspects of this invention it is desirable if the composition comprises an additional styling aid.

Particularly useful as styling aids with this invention are hair styling polymers. Hair styling polymers are well known articles of commerce and many such polymers are available commercially which contain moieties, which render the polymers cationic, anionic, amphoteric or nonionic in nature. The polymers may be synthetic or naturally derived.

The amount of the hair styling polymer may range from 0.1 to 10%, preferably 0.5 to 8%, more preferably 0.75 to 6% by weight based on total weight of the composition.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and homopolymers of N-vinylpyrrolidone having an average molecular weight of about 1,000,000 sold under the name of PVP K-120. Particularly preferred is a copolymer of polyvinyl pyrrolidone and polyvinyl acetate. An example of this copolymer is sold by BASF under the name Luviskol VA64.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic hair styling polymers are:

copolymers of N-vinylpyrrolidone and dimethylaminoethyl methacrylate, available from ISP Corporation as Copolymer 845, Copolymer 937 and Copolymer 958;

copolymers of N-vinylpyrrolidone and dimethylaminopropylacrylamide or methacrylamide, available from ISP Corporation as Styleze® CC10;

copolymers of N-vinylpyrrolidine and dimethylaminoethyl methacrylate;

copolymers of vinylcaprolactam, N-vinylpyrrolidone and dimethylaminoethylmethacrylate;

Polyquaternium-4 (a copolymer of diallyldimonium chloride and hydroxyethylcellulose);

Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;

Polyquaternium-16 (formed from methylvinylimidazolium chloride and vinylpyrrolidone), available from BASF as Luviquat® FC 370, FC 550, FC 905 and HM-552;

Polyquaternium-46 (prepared by the reaction of vinylcaprolactam and vinylpyrrolidone with methylvinylimidazolium methosulphate), available from BASF as Luviquat®Hold.

Examples of anionic hair styling polymers are:

copolymers of vinyl acetate and crotonic acid;

terpolymers of vinyl acetate, crotonic acid and a vinyl ester of an alpha-branched saturated aliphatic monocarboxylic acid such as vinyl neodecanoate;

copolymers of methyl vinyl ether and maleic anhydride (molar ratio about 1:1) wherein such copolymers are 50% esterified with a saturated alcohol containing from 1 to 4 carbon atoms such as ethanol or butanol;

acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The additional styling polymer may also contain grafted silicone, such as polydimethylsiloxane.

Specific examples of suitable anionic hair styling polymers are:

RESYN® 28-2930 available from National Starch (vinyl acetate/crotonic acid/vinyl neodecanoate copolymer);

ULTRAHOLD® 8 available from BASF (CTFA designation Acrylates/acrylamide copolymer);

the GANTREZ®ES series available from ISP Corporation esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822, 238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of suitable naturally-derived hair styling polymers include shellac, alginates, gelatins, pectins, cellulose derivatives and chitosan or salts and derivatives thereof. Commercially available examples include Kytamer® (ex Amerchol) and Amaze® (ex National Starch).

Further Components

Styling products frequently include a carrier and further additional components. The carriers and additional components required to formulate such products vary with product type and can be routinely chosen by one skilled in the art. The following is a description of some of these carriers and additional components.

The composition preferably comprises an aqueous phase. An aqueous phase thickener is preferably present and can be based on a cellulose derivative, in particular hydroxyethyl cellulose or cetyl hydroxyethyl cellulose. An alternative aqueous phase thickener is carbomer. Such aqueous phase thickeners are typically present in an amount from 0.01% to 10% by weight.

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Compositions according to the invention comprise a buffer or pH adjuster. Preferred buffers or pH adjusters include weak acids and bases such as glycine/sodium hydroxide, citric acid, triethanolamine, lactic acid, succinic acid, acetic acid and salts thereof. Frequently a mixture of buffering system is used such as sodium citrate and citric acid.

Carriers suitable for use with hair care compositions of the present invention include, for example, those commonly used in creams. The carriers used herein can include a wide range of components conventionally used in hair care compositions. The carriers can contain a solvent to dissolve or disperse the styling compound being used, with water, the $C_1$-$C_6$ alcohols, lower alkyl acetate and mixtures thereof being preferred. The carriers can also contain a wide variety of additional materials such as acetone, hydrocarbons (such as isobutane, hexane, decene), water, ethanol, volatile silicone derivatives, and mixtures thereof. The solvents used in such mixtures may be miscible or immiscible with each other.

The carrier can include a wide variety of further conditioning materials suitable for hair such as quaternary silicone polymers, silicone based conditioners and their emulsions, and amino functional silicones and their emulsions. The dynamic viscosity of these conditioning silicones is greater than 10,000 mPa·s at 35° C. and 5 s$^{-1}$.

Further general ingredients suitable for all product forms include, sun-screening agents, preservatives, anti-oxidants, anti-dandruff actives, and emulsifiers for emulsifying the various carrier components of the compositions of the invention.

The compositions of the present invention may also contain adjuncts suitable for hair care. Generally such ingredients are included individually at a level of up to 2, preferably up to 1 wt % of the total composition. Suitable hair care adjuncts include amino acids, sugars and ceramides.

Compositions of the present invention are formulated into hair care compositions, especially products with hair styling claims. The compositions are for use in styling human hair and, more preferably, they are packaged and labeled as such.

It is preferred if the products are left on hair after application and not immediately washed off.

The following non-limiting Examples further illustrate the preferred embodiments of the invention. All percentages referred to in the examples and throughout this specification are by weight based on total weight unless otherwise indicated.

Examples of the invention are illustrated by a number, comparative examples are illustrated by a letter.

EXAMPLES

| Chemical Name | Example 1 | Example A |
|---|---|---|
| Structured Oil | | |
| Tricaprylin | 22 | 26 |
| Stearalkonium Hectorite | 2.5 | 2.5 |
| propylene carbonate | 1 | 1 |
| WAX PHASE INGREDIENTS | | |
| POE(20) sorbitan monostearate | 8 | 8 |
| Sorbitan Monostearate | 2 | 2 |
| Microcrystalline wax | 23 | 0 |
| Beeswax | 13 | 0 |
| dimethylpolysiloxane | 0 | 0 |
| stearyl alcohol | 0 | 0 |
| stearyl stearate | 0 | 0 |
| hexadecyl hexadecanoate | 0 | 0 |
| white petrolatum | 6 | 0 |
| minors | 0.5 | 0.5 |
| AQUEOUS PHASE INGREDIENTS | | |
| water | 15 | 52 |
| minors | 1 | 2 |
| PVP/PVA@50% in water | 6 | 6 |
| | 100 | 100 |

The above Examples were prepared by heating the oil wax based ingredients to 50° C. and adding the stearalkonium hectorite under shear. The propylene carbonate is added post shear (5-10 min.). The resulting oil phase are added to the aqueous phase ingredients at 70° C., followed by shearing whilst cooling.

Example 1 and Example A were compared by applying each Example to half a wig. The wigs (10) were assessed by a stylist.

Example 1 was found to be easier to style hair with than Example A. Example 1 also gave better re-style results than Example A and gave the hair better volume. Neither formulation left the hands feeling sticky.

The invention claimed is:

1. A leave on hair care composition comprising
   a) a wax dispersion; and
   b) an aqueous oil emulsion wherein the oil phase is a liquid and comprises:
      i) one or more non-volatile oils selected from the group consisting of triheptanoin, tricaprylin, tricaprin, triundecanoin, trilinolein, triolein, almond oil, coconut oil, olive oil, palm kernel oil, peanut oil, sunflower oil, isopropylmyristate, isopropylpalmitate, isocetyl stearate, ethyl oleate, octyl isostearate, butyl myristate, butyl stearate, octyl palmitate, ethylhexyl cocoate, octyl dodecanol, oleyl alcohol, isostearyl alcohol, isostearic acid, mineral oil, paraffin oil, dicaprylate/dicaprate propylene glycol, $C_{12-15}$ alkyl benzoate and derivatives or mixtures thereof, where the dynamic viscosity of any single non-volatile oil or the dynamic viscosity of a blend of non-volatile oils is less than 1000 mPa·s at 35° C. and 5 $s^{-1}$;
      ii) an oil dispersible structurant selected from the group consisting of dextrin palmitate, trihydroxystearin, hydroxy stearic acid, hydrophilic hydrophobic silica, hydrophobically modified clay and derivatives or mixtures of these such that the dynamic viscosity of the structured oil phase at 35° C. prior to formation of the emulsion is at least 50,000 mPa·s at a shear rate of 0.5 $s^{-1}$ and is less than 6,000 mPa·s at a shear rate of 500 $s^{-1}$
   wherein: the emulsion further comprises a non-ionic surfactant; wax is present in an amount of from 20 to 50% by weight of the total composition; and the composition is in the form of a hair styling cream that further comprises styling polymer.

2. A hair care composition according to claim 1 in which the level of oil phase is from 15 to 50% by weight of the total composition.

3. A hair care composition according to claim 1 in which the wax of the wax dispersion comprises paraffin wax, triglyceride or mixtures thereof.

4. A hair care composition according to claim 1 in which at 35° C. the oil phase, prior to formation of the emulsion has a dynamic viscosity of at least 500,000 mPa·s at a shear rate of 0.5 $s^{-1}$ and a dynamic viscosity of 1,000 mPa·s or less at a shear rate of 500 $s^{-1}$.

5. A hair care composition according to claim 1 in which the oil phase at 35° C. prior to formation of the emulsion has a yield stress of at least 500 Pa.

6. A hair care composition according to claim 1 in which the oil phase prior to formation of the emulsion when sheared to a point past its yield point has a recovery ratio of at least 5%.

7. A hair care composition according to claim 1 in which when the structurant is a hydrophobically modified clay selected from the group consisting of stearalkonium hectorite, quaternium-18 bentonite, quaternium-18 hectorite, disteardimonium hectorite, derivatives thereof, and mixtures thereof and the oil phase further comprises a polar activator.

8. A hair care composition according to claim 1 in which the level of dispersible structurant iv) within the oil phase is from 0.5 to 20 wt % of the total oil content in the formulation.

9. A hair care composition according to claim 1 which comprises an aqueous phase structured with an aqueous phase thickener.

10. A method of treating hair comprising the step of applying to the hair a composition as defined in claim 1.

11. A manufacturing process for a composition in the form of a hair cream comprising the steps of:
    i) selecting a non-volatile oil or oils, from the group consisting of triheptanoin, tricaprylin, tricaprin, triundecanoin, trilinolein, triolein, almond oil, coconut oil, olive oil, palm kernel oil, peanut oil, sunflower oil, isopropylmyristate, isopropylpalmitate, isocetyl stearate, ethyl oleate, octyl isostearate, butyl myristate, butyl stearate, octyl palmitate, ethylhexyl cocoate, octyl dodecanol, oleyl alcohol, isostearyl alcohol, isostearic acid, mineral oil, paraffin oil, dicaprylate/dicaprate propylene glycol, C12-15 alkyl benzoate and derivatives or mixtures thereof where the dynamic viscosity of any single non-volatile oil or the dynamic viscosity of a blend of non-volatile oils is less than 1000 mPa·s at 35° C. and 5 $s^{-1}$;

ii) adding to the oil an oil dispersible structurant selected from the group consisting of dextrin palmitate, trihydroxystearin, hydroxy stearic acid, hydrophilic hydrophobic silica, hydrophobically modified clay and derivatives or mixtures of these to form a structured oil phase such that the dynamic viscosity of the structured oil phase at 35° C. prior to formation of the emulsion is at least 50,000 mPa·s at a shear rate of 0.5 $s^{-1}$ and is less than 6,000 mPa·s at a shear rate of 500 $s^{-1}$ forming an emulsion with the structured oil phase and;

iii) adding a wax to the resulting structured oil and heating;

iv) adding aqueous components to create an emulsion; and v) cooling the product;

wherein: the emulsion further comprises a non-ionic surfactant; and wax is present in an amount of from 20 to 50% by weight of the total composition.

12. Use of a hair composition according to claim 1 for styling hair, maintaining a style, enabling re-styling of hair, conditioning hair, reducing hair damage, providing hair shine, providing a wet look and/or controlling hair volume or alignment.

13. A hair care composition according to claim 1 wherein no more than 10% of the wax present in the composition is present in the emulsified oil.

14. A hair care composition according to claim 13 wherein the wax and the non-volatile oil are of a different chemical class.

15. A hair care composition according to claim 1 wherein wax is present in an amount of from 30 to 45% by weight of the total composition and the level of the oil phase is greater than 20 wt % of the total composition.

* * * * *